United States Patent [19]

Werner et al.

[11] 4,331,811

[45] May 25, 1982

[54] PREPARATION OF 2,3-DICHLORO-5-TRICHLOROMETHYL-PYRIDINE

[75] Inventors: John A. Werner, Antioch; Charles A. Wilson, Pittsburg, both of Calif.; Craig E. Mixan, Midland, Mich.

[73] Assignee: The Dow Chemical Company, Midland, Mich.

[21] Appl. No.: 243,166

[22] Filed: Mar. 12, 1981

[51] Int. Cl.³ .............................................. C07D 213/26
[52] U.S. Cl. ....................................................... 546/345
[58] Field of Search .................................. 546/345, 346

[56] References Cited

U.S. PATENT DOCUMENTS

| | | | |
|---|---|---|---|
| 3,186,994 | 6/1965 | Johnston et al. | 546/345 |
| 3,244,722 | 4/1966 | Johnston et al. | 546/303 |
| 3,420,833 | 1/1969 | Taplin | 546/345 |
| 3,538,100 | 11/1970 | Smith | 546/345 |
| 3,732,230 | 5/1973 | Brewer et al. | 546/345 |
| 4,256,894 | 3/1981 | Dietsche et al. | 546/345 |

FOREIGN PATENT DOCUMENTS 957276 5/1964 United Kingdom ................ 546/345

Primary Examiner—Alan L. Rotman

[57] ABSTRACT

Preparation of 2,3-dichloro-5-trichloromethylpyridine in high yields and purity by chlorinating 2-chloro-5-trichloromethylpyridine at 70° to 250° C. with chlorine in the presence of a catalyst containing one or more molybdenum, tungsten or ruthenium compounds.

4 Claims, No Drawings

PREPARATION OF 2,3-DICHLORO-5-TRICHLOROMETHYLPYRIDINE

BACKGROUND OF THE INVENTION

Chlorinated pyridine derivatives are known compounds and have been prepared by a number of processes. Such processes include, for example, those described in U.S. Pat. Nos. 3,420,833; 3,244,722; 3,732,230; 3,186,994; 3,538,100; British Pat. No. 957,276 and copending application 16,646 filed Mar. 1, 1979. The products of these processes have been used as herbicides and pesticides and as chemical intermediates in the preparation of other highly desired herbicide or pesticide products. Of the many chlorinated pyridine derivatives, 2,3-dichloro-5-trichloromethylpyridine is a particularly desirable intermediate for the preparation of selective herbicides having wide utility in the presence of valuable crops.

SUMMARY OF THE INVENTION

In accordance with this invention, 2,3-dichloro-5-trichloromethylpyridine is prepared in high yields and high purity by a process which comprises contacting 2-chloro-5-trichloromethylpyridine with chlorine in the presence of a catalyst at a temperature of 70° to 250° C., wherein the catalyst comprises one or more molybdenum, tungsten or ruthenium compound.

The catalysts include, for example, molybdenum, tungsten or ruthenium chlorides, bromides, oxychlorides, oxybromides, phosphines and acetates. Particularly advantageous catalysts are tungsten hexachloride, molybdenum pentachloride, tungsten hexacarbonyl, molybdenum hexacarbonyl, tungsten and molybdenum oxytetrachloride, and ruthenium chloride. The preferred catalysts are those containing tungsten or molybdenum.

The starting 2-chloro-5-trichloromethylpyridine is contacted in the liquid state with chlorine at temperatures of 70° to 250° C., preferably 150° to 200° C., and at atmospheric or superatmospheric pressures of up to about 200 psig or more, in the presence of an effective amount, advantageously about 0.01 to about 10 weight percent, preferably about 2 to about 5 weight percent, of the catalyst.

The process of the present invention is preferably conducted under essentially anhydrous conditions, and is preferably carried out in a continuous, cyclical operation, although batch operations may be employed, if desired.

DETAILED DESCRIPTION OF THE INVENTION

In carrying out the process of the present invention, gaseous chlorine is passed into the liquid 2-chloro-5-trichloromethylpyridine starting material at a temperature of at least 70° C., in the presence of the desired catalyst. At least an equimolar amount of the chlorine gas reactant is employed with from 0.3 to about 10 excess molar proportions of chlorine per mole of starting material desirably being employed. The continuous passage of excess chlorine gas through the reaction mixture serves not only to supply a large amount of reactant but to sweep out any carbon tetrachloride or hydrogen chloride by-products. The most suitable rate at which the chlorine gas is fed will vary with the reaction temperature, pressure, reaction mixture volume, etc. An excess amount of from about 0.3 to about 5.0 moles of chlorine per hour is usually employed per mole of 2-chloro-5-trichloromethylpyridine.

The degree of catalytic activity may vary depending on the reaction conditions. However, those skilled in the art can, by routine experimentation, readily determine the optimum catalyst and amount thereof required for any particular set of pressure, temperature or time conditions desired. Catalysts bonded to an inert support such as, for example, alumina, silica, silica alumina, various clays and molecular sieves are also contemplated for use in the present invention.

Generally, an increase of 10° to 15° C. in the temperature range has the effect of approximately doubling the reaction rate, while the approximate doubling in the pressure from 100 to 200 psig provides a similar response. Up to certain levels, an approximate doubling of the catalyst amount also has been found to approximately double the reaction rate.

The only constraint placed upon the superatmospheric pressures employed is one of economics, it being recognized that the cost factor for pressure equipment to allow operation above, for example, 200 psig is greatly increased and the cost may exceed any benefits obtained.

The 2-chloro-5-trichloromethylpyridine is known and can be prepared according to the methods described in the known art.

The following examples further illustrate the present invention but are not to be construed as limiting. Unless otherwise indicated, all parts are by weight.

EXAMPLE 1

A mixture of 23.1 g (0.1 mole) of 2-chloro-5-trichloromethylpyridine and 2.0 g (0.005 mole) of tungsten hexachloride was heated at 120° C. while sparging in chlorine for 42.5 hours. Vapor phase chromatography (VPC) indicated 18 percent 2,3-dichloro-5-trichloromethylpyridine. The reaction mixture was then heated to 170° to 175° C. for an additional 7 hours with the addition of chlorine and was then found (VPC) to contain about 95 percent 2,3-dichloro-5-trichloromethylpyridine.

The reaction mixture was diluted with hexane and washed with water. The organic layer was separated, dried with MgSO$_4$ and the solvent removed by evaporation to give 26.7 g of yellow liquid. Distillation gave 24.9 g of 95.6 percent 2,3-dichloro-5-trichloromethylpyridine (89.7 percent yield). The impurities were analyzed and found to be:

2,3,5,6-tetrachloropyridine (1.6%)
2-chloro-5-trichloromethylpyridine (1.6%)
2,3,6-trichloro-5-trichloromethylpyridine (1.2%)

EXAMPLE 2

Chlorine was slowly sparged into a mixture of 5773 g (25 moles) of 2-chloro-5-trichloromethylpyridine and 496 g (1.25 moles, 5 mol %) of tungsten hexachloride which was heated to 175° to 185° C. After 27.5 hours, the reaction mixture was cooled and dissolved in carbon tetrachloride. The organics were washed with a sodium carbonate solution and dried over anhydrous sodium carbonate. Evaporation of the solvent gave 6793 g of a yellow orange liquid. Analysis of the product by gas chromatography indicated 94.2 percent 2,3-dichloro-5-trichloromethylpyridine.

EXAMPLE 3

Example 1 was repeated using 25 g (0.11 mole) of 2-chloro-5-trichloromethylpyridine and 1.25 g (5 wt. %) of tungsten hexacarbonyl as the catalyst. After 16 hours of reaction, the product was worked up as in Example 2. There was obtained 18.0 g of orange yellow liquid having the following composition (internal standard gas chromatography):
2,3-dichloro-5-trichloromethylpyridine (86.06%)
2-chloro-5-trichloromethylpyridine (2.32%)
2,3,6-trichloro-5-trichloromethylpyridine (5.12%)

EXAMPLE 4

The experiment of Example 1 was repeated using 1.37 g (0.005 mole) of molybdenum pentachloride as catalyst and a temperature of 170° to 175° C. After 13.5 hours, the product was worked up and dried as in Example 1. Distillation through a Vigreux column afforded 23.5 g of a colorless liquid which was 94.5 percent 2,3-dichloro-5-trichloromethylpyridine. The impurities were analyzed and found to be:
2,3,5,6-tetrachloropyridine (1.7%)
2-chloro-5-trichloromethylpyridine (2.7%)
2,3,6-trichloro-5-trichloromethylpyridine (1.1%)

EXAMPLE 5

Example 3 was repeated using molybdenum pentachloride as the catalyst. After 8.5 hours of reaction the product was worked up as in Example 2. Obtained 20.5 g of yellow liquid having the following composition (gas chromatography):
2,3-dichloro-5-trichloromethylpyridine (95.3%)
2-chloro-5-trichloromethylpyridine (1.9%)
2,3,6-trichloro-5-trichloromethylpyridine (2.0%)

EXAMPLE 6

Example 3 was repeated using molybdenum hexacarbonyl as the catalyst. After 24 hours of reaction the product was worked up as in Example 2. There was obtained 18 g of product having the following composition (gas chromatography):
2,3-dichloro-5-trichloromethylpyridine (83.3%)
2-chloro-5-trichloromethylpyridine (2.5%)
2,3,6-trichloro-5-trichloromethylpyridine (7.6%)

EXAMPLE 7

Chlorine was slowly sparged into a mixture of 23 g (0.1 mole) of 2-chloro-5-trichloromethylpyridine and 2.5 g (10 weight percent) of molybdenum oxytetrachloride ($MoCl_4O$) and heated to 170° C. for 12 hours. The mixture of reaction products was found (gas chromatography) to have the following composition:
2,3-dichloro-5-trichloromethylpyridine (76.5%)
2-chloro-5-trichloromethylpyridine (2.0%)
2,3,6-trichloro-5-trichloromethylpyridine (1.8%)
2,3,5,6-tetrachloropyridine (11.8%)
pentachloropyridine (3.9%)
2,3,6-trichloropyridine (3.2%)

EXAMPLE 8

Chlorine was slowly sparged into a mixture of 2-chloro-5-trichloromethylpyridine (23.1 g, 0.1 mole) and ruthenium chloride (1.04 g, 0.005 mole) at 175° to 180° C. for 29.5 hours. After the reaction mixture cooled, it was diluted with toluene and the ruthenium salts which precipitated were removed by filtration. The organic layer was washed with a saturated solution of sodium chloride and dried with $MgSO_4$. Removal of the drying agent and solvent afforded a light brown liquid which upon analysis by gas chromatography was found to contain the following:
2,3-dichloro-5-trichloromethylpyridine (73%)
2-chloro-5-trichloromethylpyridine (10%)
2,3,6-trichloro-5-trichloromethylpyridine (14%)
2,6-dichloro-3-trichloromethylpyridine (2%)

Various modifications may be made in this invention without departing from the spirit or scope thereof and it is understood that we limit ourselves only as defined in the appended claims.

What is claimed is:

1. In a process for making 2,3-dichloro-5-trichloromethylpyridine by contacting 2-chloro-5-trichloromethylpyridine with chlorine in the presence of a catalyst at a temperature of 70° to 250° C., the improvement comprising employing a catalyst selected from the group consisting of tungsten hexacarbonyl or molybdenum hexacarbonyl.

2. Process of claim 1 wherein the temperature is from 150° to 200° C.

3. Process of claim 1 wherein the reaction is carried out under ambient pressure conditions.

4. Process of claim 1 wherein the reaction is carried out under elevated pressure conditions.

* * * * *